US00PP24702P3

(12) United States Plant Patent
Blake

(10) Patent No.: US PP24,702 P3
(45) Date of Patent: Jul. 29, 2014

(54) ***PROSOPIS HYBRIDA* PLANT NAMED 'AMERICAN MESQUITE'**

(50) Latin Name: *Prosopis hybrida*
Varietal Denomination: American Mesquite

(76) Inventor: Brian Edward Blake, Phoenix, AZ (US)

( * ) Notice: Subject to any disclaimer, the term of this patent is extended or adjusted under 35 U.S.C. 154(b) by 105 days.

(21) Appl. No.: 13/506,037

(22) Filed: Mar. 21, 2012

(65) Prior Publication Data

US 2013/0254949 P1 Sep. 26, 2013

(51) Int. Cl.
*A01H 5/00* (2006.01)

(52) U.S. Cl.
USPC ..... Plt./216

(58) Field of Classification Search
USPC ..... Plt./216, 226
See application file for complete search history.

*Primary Examiner* — Annette Para
(74) *Attorney, Agent, or Firm* — Christie, Parker & Hale, LLP

(57) ABSTRACT

A new and distinct variety of mesquite, botanically known as *Prosopis hybrida* and identified as 'AMERICAN MESQUITE', which is particularly characterized by its complete lack of thorns, upright branching with full foliage, rapid growth in girth and height with exceptional strength.

7 Drawing Sheets

Classification: The present invention relates to a new and distinct variety of ornamental mesquite known botanically as *Prosopis hybrida.*

Variety denomination: The new plant has the varietal denomination 'AMERICAN MESQUITE'.

BACKGROUND OF THE INVENTION

The present invention comprises a new and distinct variety of ornamental mesquite known botanically as *Prosopis hybrida*. The new variety of this tree is unusual for the species and appears to be the result of a cross between a *Prosopis alba, Prosopis chilensis, Prosopis velutina* and *Prosopis glandulosa*. It is completely thornless with very full foliage and upright branching. The characteristic of this new variety is exceptional in overall appearance and growth. The new variety was discovered as a single plant in 2005 growing on the west side of Whitfill Nursery at 2647 East Southern Ave. in Phoenix, Ariz. in a block of seedling mesquite trees being grown in containers. This new variety is not on any watering system and appears to receive irrigation only from surrounding nursery stock, which does not appear to affect its growth habit. This tree is approximately 12 years old. The original tree was found growing on its own roots.

In 2005, using *Prosopis alba* root stock, fifty (50) buds were taken from the new variety of *Prosopis hybrida* original tree and budded onto the root stock, with a 95% take in the buds. The growth habit was very vigorous, reaching an average height of 8 cm to 10 cm (3 to 4 inches) in a week from pop of bud. At two weeks, an average of 22 cm to 25 cm (8½ to 10½ inches) of growth was recorded. This growth habit continues until a height of about 100 cm (40 inches) is reached, and then some branching begins. The diameter of the trunk appears to increase in size equal to the rapid growth in height. There was no need to stake any of the new variety of budded mesquites.

In 2006, 250 trees were budded using 45 buds from the 45 clones and 205 buds from the original tree, with a 98% take on the buds. The root stock used for the 250 budded trees was

*Prosopis alba*. The growth habit of the 245 takes of the new variety budded trees was the same as the group of 45 budded trees grown in 2005.

In 2007, 2008 and 2009 groups of 500 were budded each year using 250 buds from the new variety of *Prosopis hybrida* original tree and 250 from the previous cloned group. All five generations of the new variety of *Prosopis hybrida* mesquite, asexually reproduced by budding, have maintained the outstanding characteristics of the first generation original tree which are:

Completely thornless, very full foliage with upright branching. Such budding has resulted in successful asexual propagation and the tree is stable and reproduced true to type in successive generation by such means.

SUMMARY OF THE INVENTION

A new and distinct variety of *Prosopis hybrida* American Mesquite as illustrated and described, characterized by complete lack of thorns, upright branching with full foliage, rapid growth in girth and height with exceptional strength. This is illustrated by its ability to withstand severe weather, including wind and freezing temperatures for sustained periods of time with no apparent damage and its resistance to stem canker and root rot (*phymatotrichum omnivorum*, its exceptionally full foliage and beautiful upright branching).

BRIEF DESCRIPTION OF THE PHOTOGRAPHS

DETAILED DESCRIPTION OF THE NEW VARIETY

Figure 1:
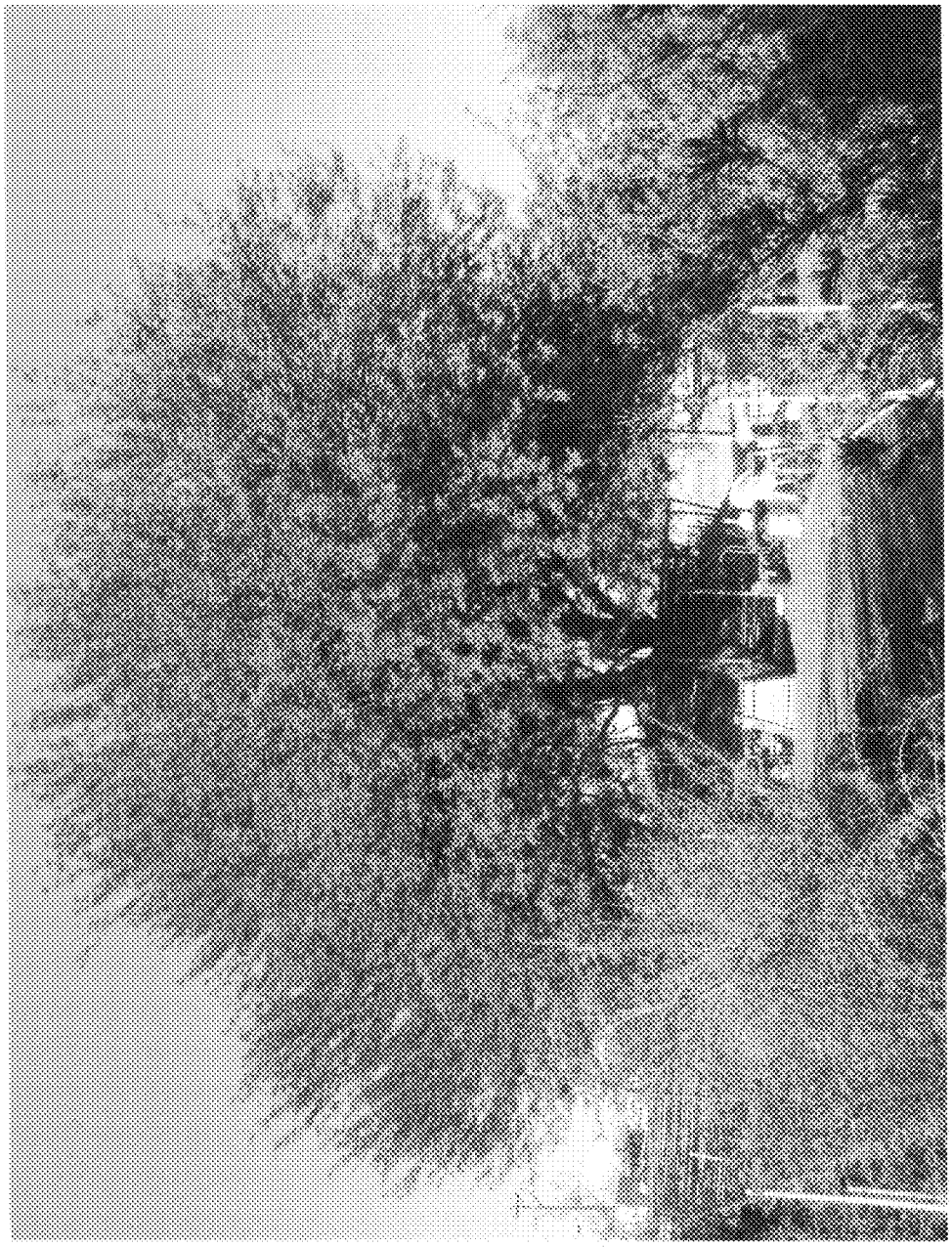
FIG. 1 is a color photograph of a mature thornless *Prosopis hybrida* tree having a 30 foot canopy.
Figure 2:
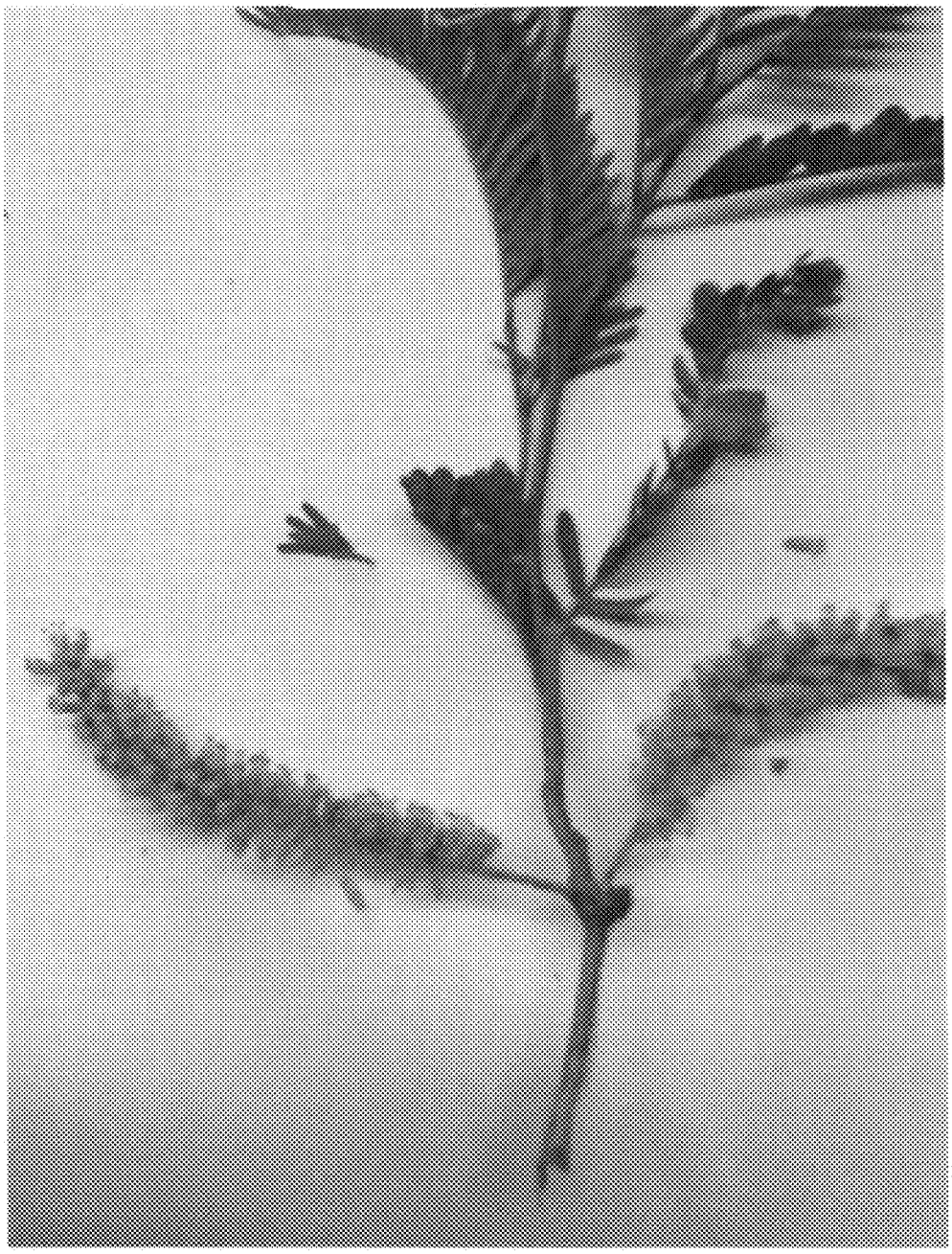
FIG. 2 is a color photograph of the buds in a spiraling pattern around the pedicel.
Figure 3:
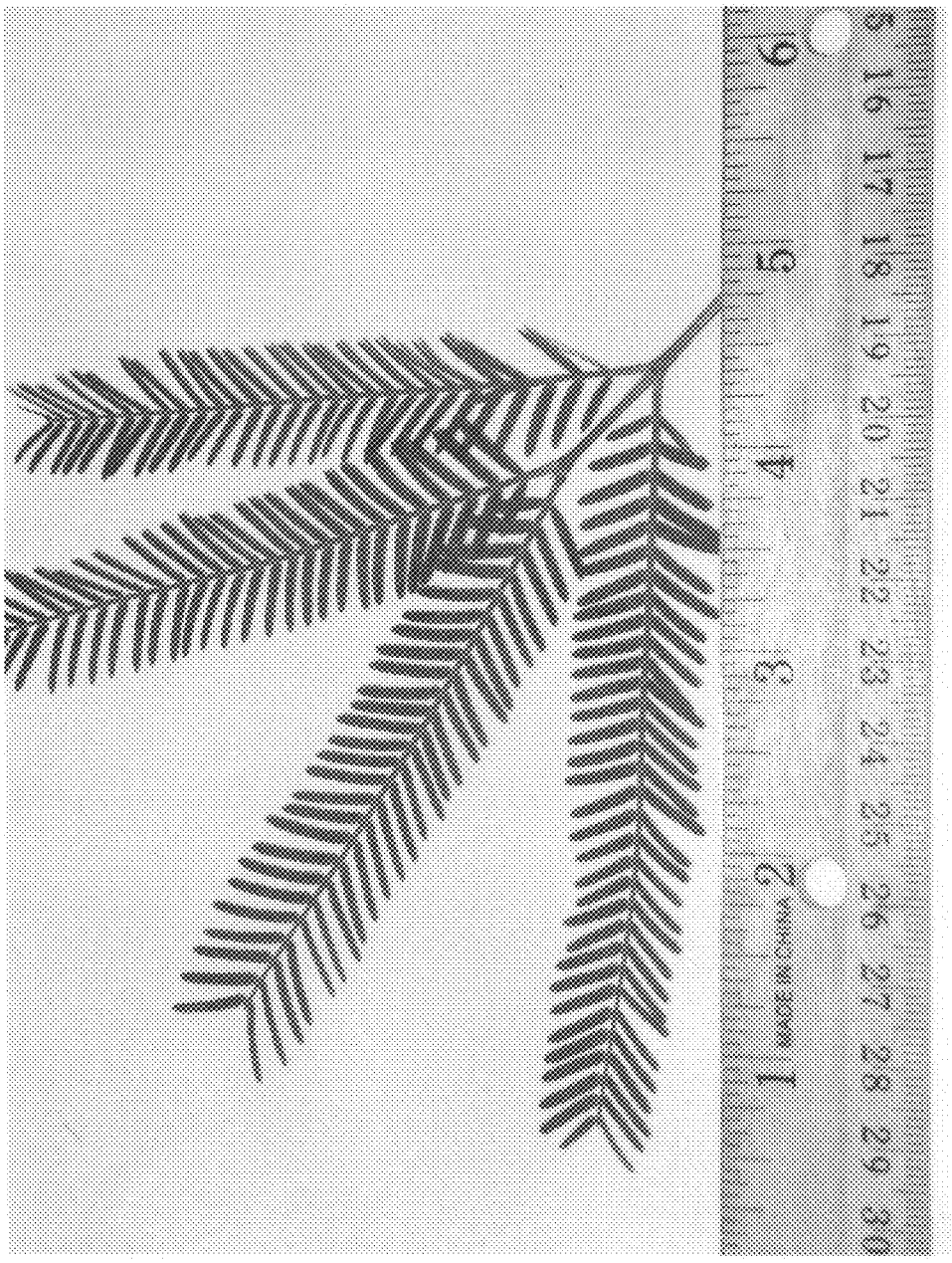
FIG. 3 is a color photograph of the pinnae length and pairs of leaflets.
Figure 4:
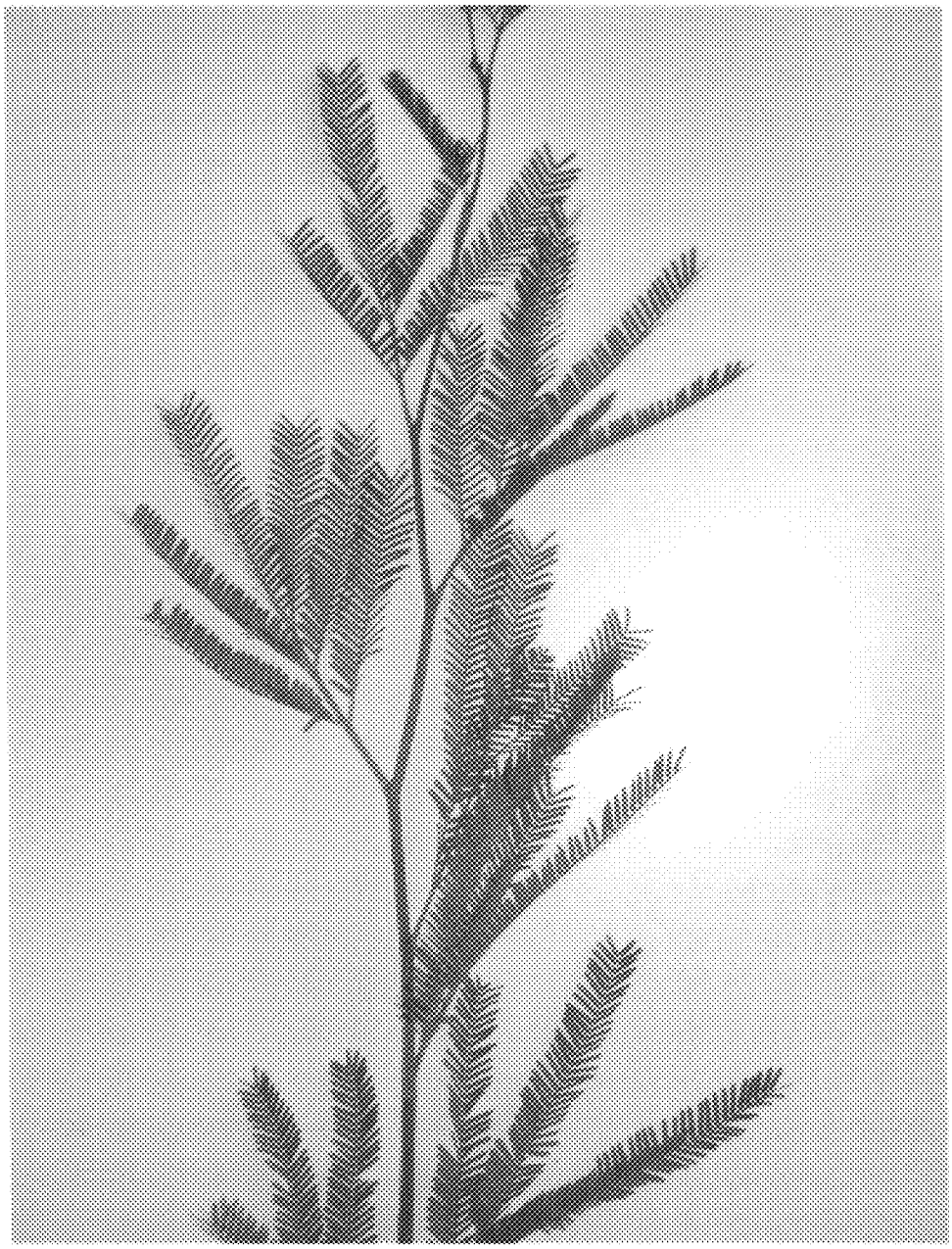
FIG. 4 is a color photograph showing one petiole from node of branch with average of six pinnae per petiole.
Figure 5:
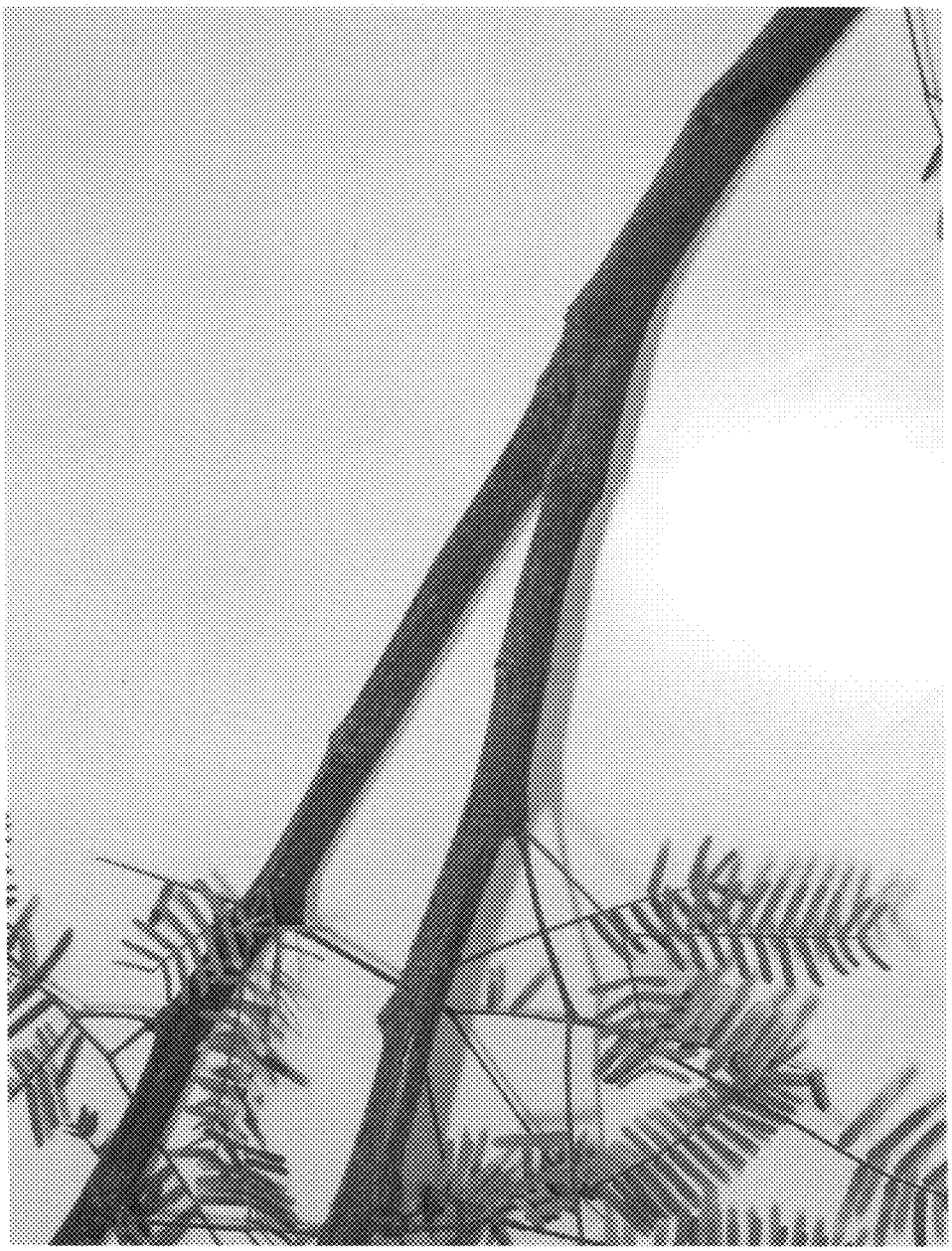
FIG. 5 is a color photograph showing young branching with smooth and dark bark.
Figure 6:
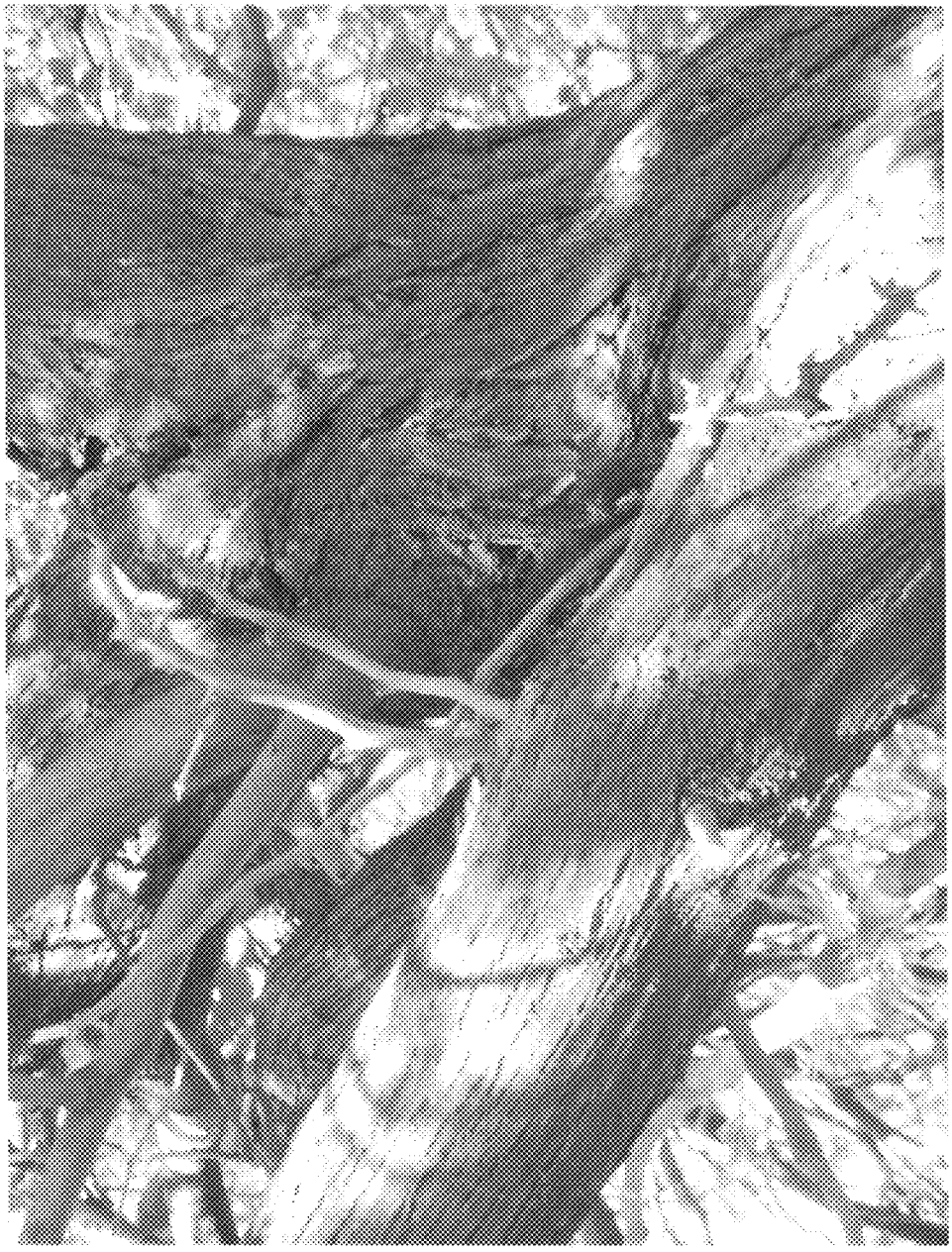
FIG. 6 is a color photograph showing the trunk and branches with coarse bark.
Figure 7:
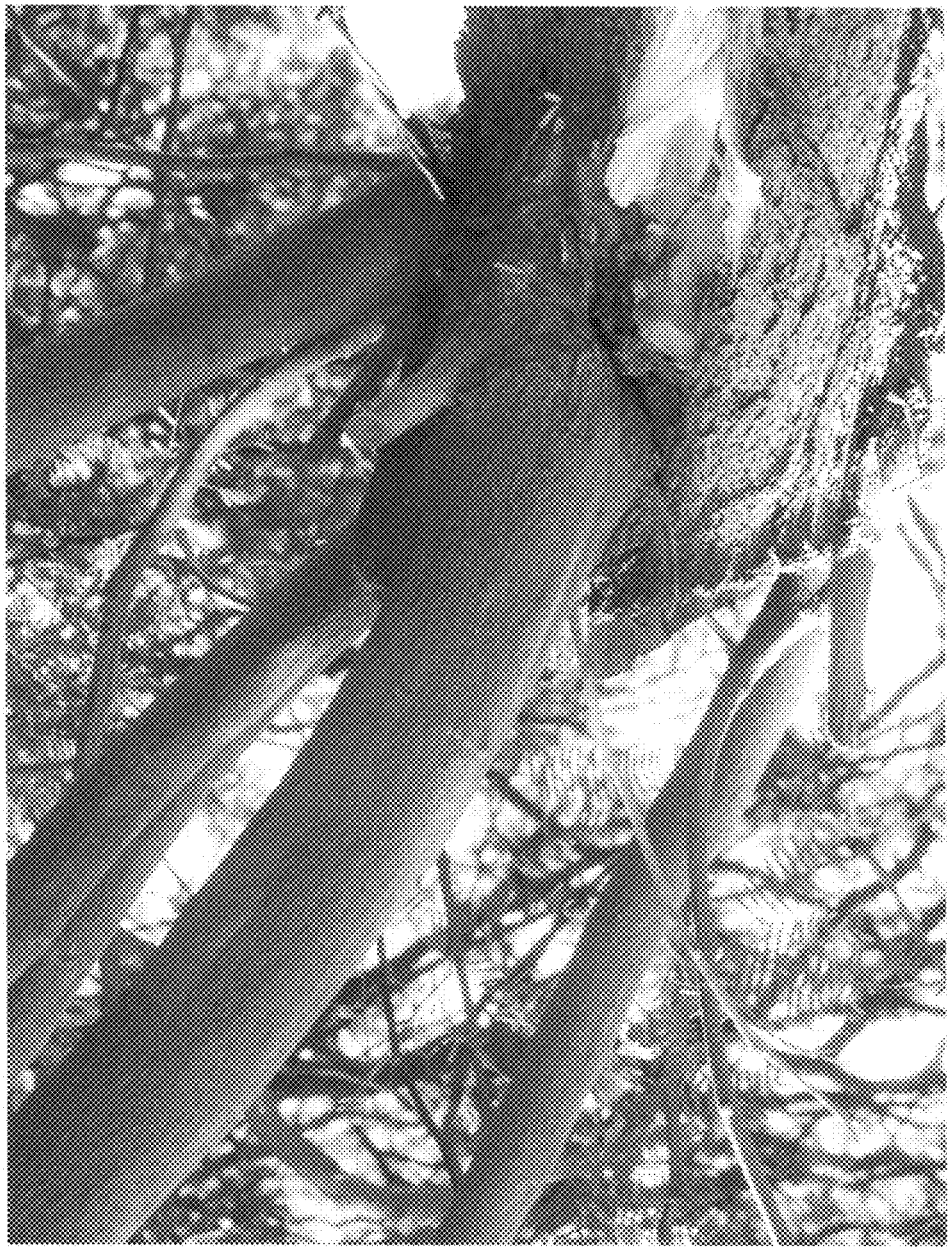
FIG. 7 is a color photograph showing trunk and branches becoming more smooth and not shaggy.

The following is a detailed description of my new variety of *Prosopis hybrida* named American Mesquite.

All color descriptions herein are made in accordance with The Colour Chart of The Royal Horticultural Society of London. The new variety of *Prosopis hybrida* is characterized by its total absence of thorns and very full foliage with upright branching, unlike the *Prosopis chilensis, Prosopis celutina* and the *Prosopis glandulosa.*

The height of the mature thornless *Prosopis hybrida* tree is approximately 30 feet high, with a canopy diameter of 30 feet. The trunk circumference is approximately 150 cm (60") one foot above the ground. The bark color of the mature mother tree trunk is group Brown 200-A. The texture of the trunk being rough and shaggy, with fissures running vertical on the trunk, about 90 cm (3') from the ground up the trunk. Most of the fissures measure approximately 4-5 mm wide 1½-2") and 23-30 cm (9-12") long showing a color of Group Greyed-Orange 165-B. At about 240 cm (8') up the trunk the fissures become smaller measuring 1-2 cm wide and 8-10 cm long and mostly disappearing beyond that. Branches 45 cm (18") in circumference are rough, but not as shaggy with a color of Group Brown-Grey 200-D. Branches 18 cm in circumference are more smooth and not shaggy with color Group Greyed-Green 197-B. Terminal branches 5 cm or less in circumference are smooth with the color Group Grey-Brown 199-A. There are no thorns present on any of the branches.

FOLIAGE

The new variety of *Prosopis hybrida* exhibits a foliage pattern an average of one petiole coming from the node of the branch, with an average of 6 pair of pinnae per each petiole. The petioles are about 5 to 6 cm long. Individual pinnae are about 10 cm to 13 cm long with an average of 27 to 30 pairs of leaflets per pinnae, spaced about ¼ cm to ½ cm apart. Each leaflet is approximately 1¼ cm to 1½ cm long and ¼ cm to ½ cm wide. The terminal branches have about 28 to 30 petioles in a distance of 98 cm (3'3") with an average of 4 cm (1½") between internodes. The color of the mature leaves, according to The Royal Horticultural Society of London Colour Chart, are Group Turquoise-Green 144-A. The new leaf or immature leaves color are Group Turquoise-Green 144-A for the upper portion and 143-C for the lower portion. The upper mature leaf is 147-B and the lower mature leaf is 146-C.

Leaflets are borne opposite, have no venation, are elongated with rounded ends and have an even margin.

SEED AND SEED POD

Mature seed pods average 11 cm to 13 cm long, 1½ cm wide and ½ cm to ¾ mm thick. Mature pods that have fallen from the tree have a curved shape and color of Group Greyed-Orange 164-C. Average number of seeds per pod are 18 to 20. Mature seeds are approximately ¾ mm long and ½ mm wide, with the shape being mostly oblong with the Color Group Greyed-Orange 164-B. Immature seed color is Group Grey-Brown 199-B.

FLOWERING

The appendage on which the bud forms are on an average 5 cm to 8 cm long and 1/16" inch in diameter, with the color Group Yellow-Green 148-D (RHC). The buds grow in a spiraling pattern around the pedicel (or stalk) and number approximately from 100 to 140 with an oval shape. When buds are mature they measure about ⅛ inch in length with the color of Group Green 138-B (RHC). When buds open the sepals (or calyx) contain approximately 5 points, measuring about ¼ cm from base to tip, forming a star shape and with the color of Group Green 138-B (RHC). An average of 10 stamen surround the stigma inside the calyx, measuring about ¼ inch or more in length with the color Group Yellow-Orange 20-A (RHC). The bloom is approximately 4-5 cm (1½-2") long and 1¼ cm wide, with the color of Group Yellow-Orange 20-B (RHC). The observed bloom time is in March and April in Phoenix, Ariz. and have a mild, sweet fragrance

THORNS

The *Prosopis hybrida* mesquite has proven completely thornless from six (6) years of first generation and five (5) generations of asexually reproduction by budding from each generation. No thorns appeared at any stage of growth, nor did any develop into maturity. This distinguishing characteristic, thornless and no developing thorns, is in contrast to crosses of the *Prosopis chilensis*, the *Prosopis velutina* and the *Prosopis glandulosa* which are prone to develop thorns.

DISEASE RESISTANT

Since 2005 no stem cankers were ever observed on new variety of *Prosopis hybrida* Mesquite original tree or any of the clones. Cotton root rot (*Phymatotrichum Omnivorum*) does not appear to affect this tree.

COLD HARDY

In 2006 an extremely hard freeze of a 16 degree low was experienced. No apparent damage was sustained to the original tree with only the tips of top terminal branches freezing. The tree still retained over 60% of its leaves. Young trees also had the tips of the branches nipped and about 40% of their foliage lost. With winds sustained at 60+ mph no apparent damage was sustained by the original tree or the young budded trees.

I claim:

1. A new and distinct variety of *Prosopis hybrida* identified as 'AMERICAN MESQUITE' as illustrated and described, characterized by complete lack of thorns, upright branching with full foliage, rapid growth in girth and height with exceptional strength.

* * * * *

UNITED STATES PATENT AND TRADEMARK OFFICE

CERTIFICATE OF CORRECTION

PATENT NO. : PP24,702 P3
APPLICATION NO. : 13/506037
DATED : July 29, 2014
INVENTOR(S) : Brian Edward Blake It is certified that error appears in the above-identified patent and that said Letters Patent is hereby corrected as shown below:

On the Title Page

(54) Title Delete "PLANT"

Signed and Sealed this
Twenty-eighth Day of June, 2016

Michelle K. Lee

Michelle K. Lee
*Director of the United States Patent and Trademark Office*